United States Patent [19]

Woinowski

[11] 4,277,432
[45] Jul. 7, 1981

[54] METHOD FOR EXTRUDING CATHETER TUBING

[75] Inventor: Willis E. Woinowski, Racine, Wis.

[73] Assignee: Vesta, Inc., Milwaukee, Wis.

[21] Appl. No.: 89,506

[22] Filed: Oct. 30, 1979

[51] Int. Cl.³ ............................................... B29F 3/10
[52] U.S. Cl. .................................... 264/173; 128/348;
128/349 R; 264/174; 264/209.8; 264/236;
425/113
[58] Field of Search ............... 264/173, 174, 209, 236;
425/113, 114, 380, 467; 128/348, 349 R

[56] References Cited

U.S. PATENT DOCUMENTS

| | | | |
|---|---|---|---|
| 2,268,321 | 12/1941 | Flynn | 264/209 |
| 3,405,426 | 10/1968 | Donald | 425/114 |
| 3,508,554 | 4/1970 | Sheridan | 264/209 |
| 3,692,448 | 9/1972 | Menasoff | 425/113 |
| 3,712,770 | 1/1973 | Arnaudin, Jr. | 264/174 |
| 3,719,444 | 3/1973 | Benjamin et al. | 264/174 |
| 3,856,447 | 12/1974 | Schiesser | 264/174 |
| 4,105,732 | 8/1978 | Slingluff | 264/173 |

Primary Examiner—Jeffery R. Thurlow
Attorney, Agent, or Firm—Andrus, Sceales, Starke & Sawall

[57] ABSTRACT

Method and apparatus for making hollow catheter tubes or tubing from silicone rubber in which silicone rubber X-ray opaque flexible thread is introduced into a wall of the tubing during the extrusion of the tubing. The flexible thread enters the extruded silicone rubber in the extruding die close to the outer diameter of the tube at a line where the extruded silicone material changes from a varying to a constant cross-section. The apparatus is constructed to locate the terminating forward end of the tube through which the silicone thread passes at a line at the entrance to the constant cross-sectional area. The extruded tubing with the thread in one wall thereof is then cured into a final product.

5 Claims, 3 Drawing Figures

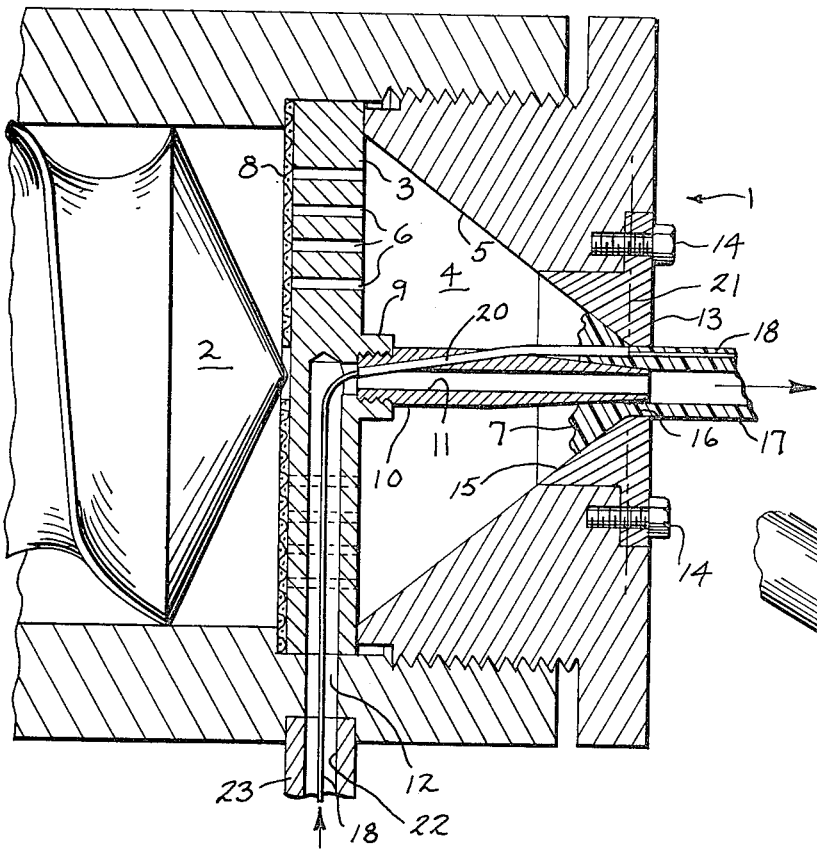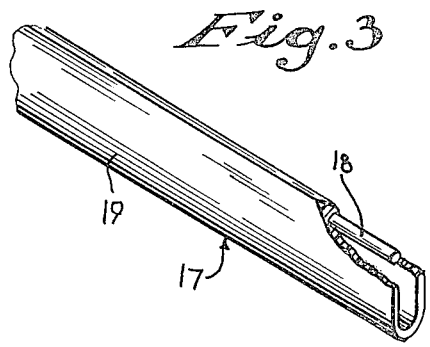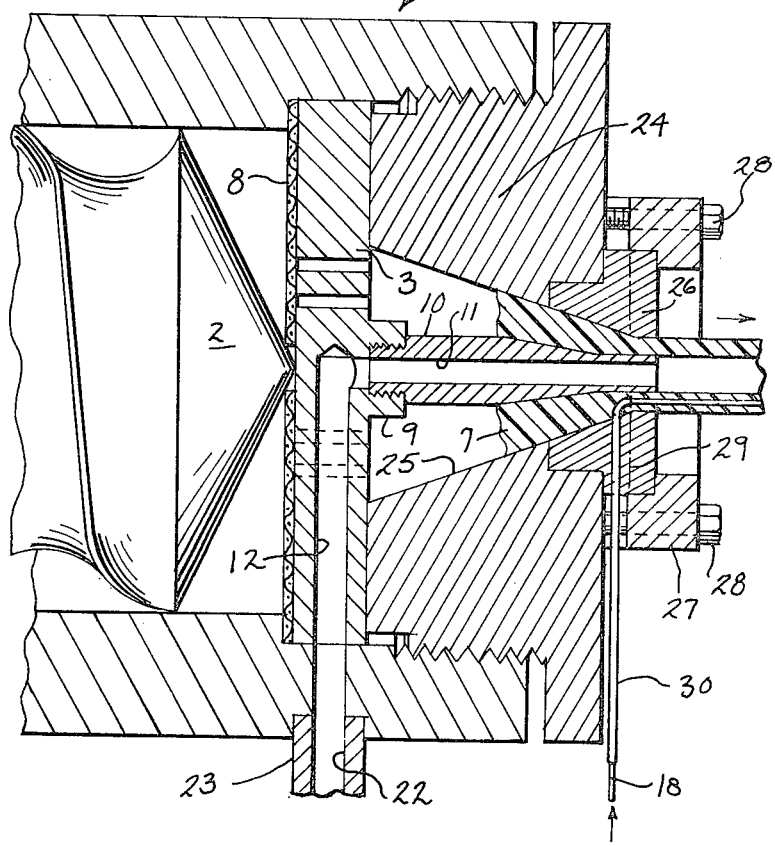

4,277,432

METHOD FOR EXTRUDING CATHETER TUBING

BACKGROUND OF THE INVENTION

The invention is directed to tubes for use as catheter tubes or the like of varying shapes and sizes which are ordinarily employed by medical personnel to drain fluids from body cavities or to distend body passages. It is desirable to know the location of the tube within the body. Elastomeric material such as silicone rubber is extruded to form the tube and simultaneously a silicone X-ray opaque thread is introduced into one wall of the tube as the latter is extruded which readily is exposed when the tube is located in a body and is X-rayed. The method and apparatus produces an extremely effective working catheter tube or the like.

SUMMARY OF THE INVENTION

There is provided by this invention a hollow tube or tubing of inherently flexible elastomeric material such as, for example, silicone rubber of varying sizes and shapes by an extrusion operation followed by curing to complete the tubes.

To provide an X-ray marking member in the tubing, a thread-like member, also of inherently flexible elastomeric X-ray opaque material, such as silicone rubber, is introduced into the outer diameter of a wall of the tube during the extrusion operation at a line at which the die of the extrusion apparatus changes from a varying extent to a constant extent.

After the extrusion of tubing and the introduction of the thread, which may be of various colors, the tubing is cured into a final product.

The invention has several embodiments. Under the first embodiment the flexible elastomeric thread is introduced into the tubing extruding material via a guide tube extending through an extruding pin or inner die which forms the hollow inside of the tubing.

In the second embodiment, the tubing which carries the flexible elastomeric thread extends through the outer extruding die rather than through the extruding pin.

BRIEF DESCRIPTION OF THE DRAWINGS

FIG. 1 is an enlarged diagrammatic view of an extruder and extruder die, and illustrates an embodiment of the apparatus of the invention in which the thread guide tube extends through the extruding pin;

FIG. 2 is an enlarged diagrammatic view of the extruder and extruder die with the thread guide tube extending within the extruder die; and FIG. 3 is a perspective view of the tube extruded by the method and apparatus of the invention with parts broken away to illustrate the thread disposed therein after the extrusion operation.

DESCRIPTION OF THE PREFERRED EMBODIMENT

Referring to FIG. 1 there is shown an extruder 1 within which is located an extruding screw 2 and an adjustable breaker plate 3 disposed forwardly of screw 2. Extruder 1 extends forwardly of breaker 3 and has a conical shaped hollow opening 4 formed by the extruder member 5 threaded into the body of extruder 1 and having an inner downwardly tapered wall.

The breaker plate 3 has a plurality of apertures 6 extending therethrough to provide passages for the flow of the extruded material shown in part at 7 in FIG. 1. The inner side of breaker plate 3 is covered by a screen 8 to thereby remove undesirable deposits from the extruded material.

Breaker plate 3 has an internally threaded forwardly extending collar 9 located generally centrally of the forward side of breaker plate 3 and within which is threaded the forwardly extending extruder pin 10 which terminates commensurate with the forward end of extruder 1 and operates as an inner die. Pin 10 has a central passage 11 therethrough which connects with the vertical passage 12 through breaker plate 3 and extruder 1 for flow of air.

The forward end of extruder 1 which initially is open, surrounds extruder pin 10 and receives an outer extruder die 13 which is secured by bolts 14 to the forward end of extruder 1. Die 13 surrounds pin 10 and has a conical inner surface 15 tapered in line with and in accord with the downwardly tapered extruder member 5 of extruder 1. The conical varying cross-section of the inner surface 15 of die 13 terminates generally abruptly in a straight extending surface 16 having a constant cross-section which extends forwardly of extruder 1 and surrounds the outer end portion of pin or inner die 10 in predetermined spaced relation therewith. The spacing between die 13 and pin 10 regulates the thickness of the wall of the tube 17 which is extruded between pin 10 and die 13. Tube 17 is of an elastomeric material such as silicone and may be of various shapes such as oblong, round and the like.

In order to encase a flexible marking thread 18 in the wall 19 of the tube 17 as tubing 17 is extruded, a passage or guide tube 20 is provided in the wall of extruder pin 10. Tube 20 at the outer end extends through and out of the wall of pin 10 and terminates in the area of line 21 which is the dividing line between the tapered and varying surface 15 of extruding die 13 and the constant or straightly extending surface 16 of extruding die 13. This introduces marking thread 18 into extruded material 7 at that critical area. If thread 18 is introduced too far before line 21, the raw extruded material 7 tends to enter guide tube 20 and block guide tube 20 which can cause thread 18 to stretch as the extrusion operation proceeds. If marking thread 18 is introduced too far beyond line 21, air may enter extruded material 7 with thread 18 and produce an undesirable air passage in catheter tube 17 adjacent to thread 18. Both of the described undesirable introductions of thread 18 into extruded material 7 creates an extruded tube 17 which must be rejected.

Thread 18 may be of any color and by way of example a blue color has been found to be very satisfactory. Thread 18 which may be radio-opaque elastomeric material such as silicone is very flexible and is only partially cured when introduced into the wall of tube 17 so that a good bond is obtained between thread 18 and tube 17 when tubing 17 is finally cured. The thread 18 being of a flexible nature and not stiff enough to be forced into die 13 so that when the extruder 1 is placed in operation the extrusion operation tends to automatically draw thread 18 into the wall of tube 17 as the latter is extruded. For example, thread 18 may have a diameter of approximately 0.040 of an inch and a hardness of 30 to 60 Durometer Shore A scale.

The rear portion of guide tube 20 projects from extruder pin 10 into central passage 11 within the area of collar 9 of breaker plate 3 to receive thread 18 from the vertical passage 12 of breaker plate 3 arriving from a source, not shown. Passage 12 is aligned with the passage 22 extending through a guide member 23 secured to extruder 1.

After tube or tubing 17 with thread 18 encased in the wall 19 is extruded the tubing 17 is then heated to partially cure tubing 17 and thread 18 and then is baked for four or five hours to complete the cure and bond thread 18 to tubing 17. The tubing 17 may then be cut into the lengths of tubes 17 desired.

FIG. 3 illustrates a tube or tubing 17 and thread 18 shown as it projects from the wall of tube 17 which has been partially broken away. The edge of the tubing 17 may be notched if desirable.

FIG. 2 is directed to another embodiment of the invention. This embodiment has the usual extruder 1 enclosing screw 2 and breaker plate 3 and screen 8 with plate 3 having passage 12 extending therethrough and through extruder 1 to entry passage 22 for flow of air. Similarly, extruder pin 10 is threaded into central collar 9 of breaker plate 3 and extends forwardly and has a hollow central passage 11 therein for receipt of air from passage 12.

Forwardly of breaker plate 3 extruder 1 in general is open and in which is lodged an extruder member 24 having a conical inner downwardly tapered surface 25. The extruding die 26 is disposed within the forward end of extruder 1 and is secured to member 24 by a ring 28 through which extend the bolts 28 and into threaded engagement with extruder member 24.

Extruding die 26 tapers downwardly in line with the tapered surface 25 of extruder member 24 and in general abruptly changes from a varying extent to a straight line extent at line 29 around the outer end portion of extruder pin 10.

In this embodiment guide tube 30 extends vertically through extruding die 26 and then turns forwardly so that the marking thread 18 is discharged into the extruded material 7 at line 29 in the area where die 26 rather abruptly changes from the varying extent to a constant or straight line extent. This overcomes the problems discussed with respect to the first embodiment caused by entry of thread 18 into the extruded material too soon or too late.

The tubing 17 provided by the second embodiment is then cured to complete the tube and encasing of thread 18.

The invention provides a method and apparatus for introducing an X-ray opaque marking thread or line into the wall of a catheter tube or tubing whereby rejection of the tubing for use for medical purposes is kept to a minimum.

Various modes of carrying out the invention are contemplated as being within the scope of the following claims particularly pointing out and distinctly claiming the subject matter which is regarded as the invention.

I claim:

1. In a method of encapsulating a flexible preformed incompletely cured marking thread of X-ray opaque elastomeric material into the wall of tubing of elastomeric material during an extrusion operation which comprises, the steps of extruding the tubing elastomeric material through an opening between a pair of dies in a flow path initially varying in cross-section in a downward extent and then terminating into a flow path having a constant cross-section area, and introducing the thread of elastomeric material into the elastomeric material disposed to form the tube in the area of the dividing line wherein the flow path of the extruder tubing material changes from varying to constant to prevent blocking of the passage through which the thread is introduced into the extruded material with consequent stretching of the thread, or prevent entry of air into the extruded elastomeric material and the consequent forming of undesirable air passages adjacent to the thread in the final tubing and fully curing the tubing and thread to complete the tubing and the encapsulating of the marking thread in the wall of the tubing.

2. The method of encasing a flexible preformed incompletely cured thread of X-ray opaque elastomeric material into the wall of tubing of elastomeric material during an extrusion operation as set forth in claim 1, and the area in the flow path of the extruder tubing material wherein the path changes from varying to a constant extent is at a line across the path of the flow of material in the area of change of flow of the tubing extruded material.

3. The method of encasing a flexible preformed incompletely cured thread of X-ray opaque elastomeric material into the wall of tubing of elastomeric material during the extrusion as set forth in claim 1, and the elastomeric material of the thread and tubing being silicone.

4. The method of encasing a flexible preformed incompletely cured marking thread of X-ray opaque elastomeric material into the wall of tubing of elastomeric material during an extrusion operation as set forth in claim 1, and the flexibility of the marking thread being of an order preventing introduction of the thread into the tubing extrusion material when the extrusion operation is being carried out, and commencement of the extrusion operation effecting drawing of the thread into the tubing as the extrustion operation is begun and proceeds.

5. The method of encasing a flexible preformed incompletely cured marking thread of X-ray opaque elastomeric material into the wall of tubing of elastomeric material during an extrusion operation as set forth in claim 1, and the marking thread having a diameter less than the tubing wall thickness and a hardness measurement similar to the cured tubing hardness.

* * * * *